「12」 United States Patent
Corsini et al.

(10) Patent No.: US 9,101,148 B2
(45) Date of Patent: Aug. 11, 2015

US009101148B2

(54) CARBOHYDRATE MODIFYING AGENT AND DRINKS CONTAINING THE MODIFYING AGENT

(75) Inventors: Frank Corsini, East Dennis, MA (US); Richard Kozlenko, San Rafael, CA (US)

(73) Assignee: SBS Food Group LLC, Lexington, MA (US)

( * ) Notice: Subject to any disclaimer, the term of this patent is extended or adjusted under 35 U.S.C. 154(b) by 519 days.

(21) Appl. No.: 12/661,092

(22) Filed: Mar. 10, 2010

(65) Prior Publication Data

US 2010/0172887 A1 Jul. 8, 2010

Related U.S. Application Data

(63) Continuation-in-part of application No. 12/319,644, filed on Jan. 9, 2009, now abandoned, which is a continuation-in-part of application No. 10/155,865, filed on May 24, 2002, now abandoned.

(60) Provisional application No. 60/293,657, filed on May 25, 2001.

(51) Int. Cl.
| | |
|---|---|
| *A61K 36/54* | (2006.01) |
| *A61K 36/87* | (2006.01) |
| *A61K 36/185* | (2006.01) |
| *A23C 9/13* | (2006.01) |
| *A23L 1/09* | (2006.01) |
| *A23L 1/236* | (2006.01) |
| *A23L 1/30* | (2006.01) |
| *A23L 1/302* | (2006.01) |
| *A23L 1/304* | (2006.01) |
| *A23L 1/305* | (2006.01) |
| *A23L 1/308* | (2006.01) |
| *A23L 2/52* | (2006.01) |
| *A23L 2/54* | (2006.01) |
| *A23L 2/66* | (2006.01) |

(52) U.S. Cl.
CPC .............. *A23C 9/13* (2013.01); *A23C 9/1307* (2013.01); *A23C 9/1322* (2013.01); *A23L 1/09* (2013.01); *A23L 1/236* (2013.01); *A23L 1/3002* (2013.01); *A23L 1/302* (2013.01); *A23L 1/304* (2013.01); *A23L 1/308* (2013.01); *A23L 1/3014* (2013.01); *A23L 1/3051* (2013.01); *A23L 1/3055* (2013.01); *A23L 1/3081* (2013.01); *A23L 2/52* (2013.01); *A23L 2/54* (2013.01); *A23L 2/66* (2013.01); *A23V 2002/00* (2013.01)

(58) Field of Classification Search
CPC ................. A23V 2002/00; A23V 2250/708; A23V 2250/161
USPC ......................................... 424/725, 439, 400
See application file for complete search history.

(56) References Cited

U.S. PATENT DOCUMENTS

| 5,445,837 | A | * | 8/1995 | Burkes et al. .................. 426/74 |
| 6,143,340 | A | * | 11/2000 | Huang .......................... 426/466 |
| 6,531,126 | B2 | * | 3/2003 | Farmer ......................... 424/115 |
| 2003/0031758 | A1 | * | 2/2003 | Koss et al. ..................... 426/72 |
| 2003/0049208 | A1 | * | 3/2003 | Ream et al. .................... 424/48 |

FOREIGN PATENT DOCUMENTS

| JP | 06327434 A | * | 11/1994 |
| JP | DW 1995-047865 | * | 11/1994 |

\* cited by examiner

*Primary Examiner* — Chris R Tate
*Assistant Examiner* — Randall Winston

(57) ABSTRACT

A carbohydrate modifying formulation that modulates the rate of sugar absorption and/or metabolism in a subject to whom the formulation is administered. In one embodiment, the formulation comprises an active soluble fiber, one or more polyphenolic compounds, an aqueous diluent, and sugar. In another embodiment, the formulation is a dry powder that comprises an active soluble fiber, antioxidant containing botanical extracts, crystalline fructose, a probiotic, vitamins and minerals.

3 Claims, No Drawings

CARBOHYDRATE MODIFYING AGENT AND DRINKS CONTAINING THE MODIFYING AGENT

CROSS-REFERENCES TO RELATED APPLICATIONS

The present application is a continuation-in-part of U.S. patent application Ser. No. 12/319,644, filed on Jan. 9, 2009 now abandoned, which is a continuation-in-part of U.S. patent application Ser. No. 10/155,865, filed on May 24, 2002 now abandoned, which in turn claims priority under 35 U.S.C. 119(e) from U.S. Provisional Patent Application No. 60/293,657, filed on May 25, 2001.

BRIEF SUMMARY OF THE INVENTION

The present invention provides a carbohydrate modifying formulation or agent of synergistic ingredients, pertaining to the metabolism of mono and disaccharides. Metabolically, the formulation of the invention slows the absorption of sugars, modifies the release of insulin, and stabilizes blood sugar response. Additionally, the oral ingestion of the formulation of the invention prevents or reduces the formation of dental caries by inhibiting the metabolic capability of dental plaque-forming bacteria to convert sugars into erosive, tooth-decaying acids.

The formulations of the invention provide direct and indirect positive effects on sugar metabolism and blood sugar response. Thus, the formulations of the invention, when consumed in normal amounts, do not adversely contribute or aggravate such conditions as obesity, diabetes, or dietary-based, hormone related hyperactivity such as that often described in young children.

A formulation of the invention may be in liquid or dry form. That is, it may be in the form of a powder that comprises or contains the formulation, or in the form of a liquid, either an aqueous liquid or a non-aqueous liquid. In one preferred aspect, the invention provides a finished, water-based beverage, into which the formulation of the invention is incorporated. Moreover, the invention provides a finished water-based beverage, which is acidified and which includes a formulation of the invention.

The invention also includes a method of slowing absorption of sugars, for instance, from the intestine of a subject (including but not limited to a human individual), that comprises administering to the subject, or making available for ingestion by the mammal, a formulation of the invention. The formulation becomes effective when in an aqueous medium, which may be provided extrinsically, for instance by oral or intravenous administration or ingestion of an aqueous liquid containing the formulation, or intrinsically, for instance by ingestion of a solid formulation of the invention which is acted on by the body's digestive secretions and conveyed to and through the body's digestive system (an aqueous environment).

Additional objects and advantages of the invention will be apparent from the detailed description as follows:

DETAILED DESCRIPTION OF THE INVENTION AND THE PREFERRED EMBODIMENTS

The present invention provides a formulation having desirable properties built upon synergistic ingredients; maintaining low simple sugar levels; and slowing down the normally rapid absorption of simple sugars from the gut. This objective best optimizes energy levels by thwarting the potential destabilizing effects on blood sugar and insulin response, by preferably utilizing a polysaccharide matrix of complex carbohydrates and soluble gum fibers.

The invention provides numerous advantages not found in other agents including, but not limited to, limiting the effects of excessive use of ingredients, such as sugar, that may promote greater oxidative stress and actually reduce energy. Ingredients are preferably chosen from among those that neutralize and inhibit free radical production and oxidative stress and, therefore, help to protect the cellular energy generating mechanisms. Moreover, presently preferred ingredients are those that assist in the cellular utilization and burning of fuels for energy. The composition of the invention also provides multiple tiered uses of various timed caloric energy fuels plus the sweetness system disclosed herein for longer, sustained energy.

The present invention provides compositions of active and, optionally, inactive ingredients. The compositions can be prepared in any form including, but not limited to, dry formulations, aqueous formulations, and the like. The compositions of the invention can be included in substantially any manufactured foodstuff or beverage. When consumed simultaneously or in time proximity with other foods that contain sugars, the carbohydrate modifying effects of the compositions will extend to and similarly influence those sugars that are undergoing digestion and assimilation.

A presently preferred embodiment of the composition includes one or more polyphenolic compounds. While not being bound to any particular theory of operation, the inventors presently prefer polyphenolic compounds that inhibit the digestive enzymes amylase (starch digestion) and sucrase (sugar digestion), thereby slowing sugar absorption, and reducing overstimulation of the insulin response, and the subsequent modification of sugar metabolism.

Moreover, preferred polyphenolic compounds inhibit the activity of the bacterial enzyme, glucan transferase, which metabolizes simple sugars as found in beverages, into sticky dental plaque. Without the sticky plaque present, the bacteria cannot adhere to the tooth surfaces, ferment the sugars into acids, and create dental caries.

Polyphenolic compounds of use in the present invention are isolated from any convenient source. Preferred polyphenolic compounds include catechins, tannin extracts, extracts of Camellia Sinesis (e.g. green and black teas), and those found in cranberry, aronia berry, bilberry, and grape seed. Other useful sources of polyphenolic compounds will be apparent to those of skill in the art.

Preferred green tea and black teas actives are the catechins and the aflavins.

The polyphenols can be present in the formulation in any useful amount, but they are preferably present in an amount of from about 0.2 mg to about 500 mg (in 8 oz of water or other water or other diluent, when a diluent is used), preferably from about 10 to about 500 mg.

The formulations of the invention also preferably include one or more amino acid or source of amino acid, preferably selected from soy, soy sprouts or other legume derived proteins such as mung bean, or dairy based protein, amino chelated minerals, and whey or other dairy-based proteins. Other useful sources of amino acid are known to those of skill in the art.

The amino acids of use in the present invention are preferably free amino acids, most preferably free glycine and arginine, which lower blood sugar levels by virtue of mild inducement of insulin release from the pancreas. Arginine, independent of insulin release, also stimulates release of GH (growth hormone) from the pituitary gland. GH is a natural counterbalance to the excessive hypoglycemic effects of insulin. Moreover, glycine, independent of energy dynamics, is an amino acid neurotransmitter substrate, that is described in the scientific literature as being inhibitory to neurological hyperactivity.

Thus, a presently preferred source of amino acid is soy protein, which is a rich source of glycine and arginine, improves glucose tolerance and peripheral insulin sensitivity which is crucial for blood sugar stability.

The one or more amino acid can be present in the composition in any useful amount, but is preferably present in an amount of from about 5 mg to about 10 grams (per 8 ounces of water or other diluent, when a diluent is used) preferably from about 200 mg to about 10 grams. When the amino acid is provided by a source of amino acid, other than the free amino acid, the source is preferably present in an amount that provides the preferred amount of the free amino acid.

Also present in preferred formulations of the invention is soluble fiber, preferably active soluble fiber. As used herein, "active soluble fiber" refers to soluble fiber that is biologically responsive to bacteria in the mammalian GI tract and/or participates in one or more blood sugar modifying mechanism in vivo. The soluble fiber is from any source, however, preferred fibers are those that participate in one or more blood sugar modifying mechanism, such as: (1) conversion of the soluble fiber into short chain fatty acids (SCFAs) by the intestinal bacteria (SCFA, particularly propionic acids, increase glycolysis and reduces gluconeogenesis thus normalizing blood sugar); and (2) slowing the absorption of sugar from the intestinal tract by solution fiber; which ultimately influences the rate of sugar metabolism.

Additionally, antioxidants, including phenolic-based botanical extracts are optionally included as a component of the present formulation. The presence of the antioxidant can aid in overcoming or blunting the pro-oxidant and destabilizing hypoglycemic effects of quickly absorbed simple sugars found in most commercial beverages.

Presently preferred soluble fibers having the above-described characteristics include, inulin, FOS (fructo-oligosaccharides e.g. Belaflora™), and gums.

The soluble fiber is present in any useful amount, but is preferably present in any amount of from about 100 mg to about 8 grams (per 8 ounces of water or other diluent, when a diluent is used), preferably from about 500 mg to about 8 grams. In those embodiments in which 5 grams or more soluble fiber is present, the composition of the invention is preferably able to reduce the post prandial rise in blood sugar levels.

In another preferred embodiment of the invention, the formulation includes one or more zinc salt or other source of the zinc ion. Metabolically, zinc is a critical nutrient in the synthesis of insulin and the metabolism of carbohydrates. From a dental perspective, cariogenic bacteria enzymatically produce an insoluble glucan deposit from simple sugars present in the mouth that firmly adheres to the enamel tooth surface. Original study at UCSF School of Preventative Dentistry by the present inventors, demonstrated that two tested zinc salts, 0.5% zinc solution (zinc chloride) and same concentration of zinc ascorbate, both inhibited the growth and adherence of mutans streptococci in vitro. This demonstrates that the zinc cation, not the counter ion, is the most significant portion of the salt molecule for this function.

Preferred sources of the zinc ion include zinc chloride, zinc sulfate, zinc ascorbate, zinc picolinate, zinc amino acid chelates, and zinc-EDTA.

The zinc salt(s) is present in any useful quantity, but is preferably present in an amount of from about 1 mg to about 40 mg (per 8 ounces of water or other diluent, when a diluent is used).

In another preferred embodiment, the invention provides an acidic finished drink composition. The drink is preferably water-based. The water used to formulate the drink can be, for example, still, carbonated, or dairy-based. The pH of the finished drink is preferably from about 1 to about 7, more preferably from about 1 to about 5, and more preferably from about 1 to about 3. The solubility and assimilation of mineral salts, especially divalent minerals such as calcium, zinc, magnesium, iron, are enhanced in an acidic medium. These elements have many important roles relating to cellular metabolism and tissue structure.

The acid or source of acid includes both organic and inorganic acids. Exemplary organic acids include phosphoric acid.

The source of the sugars relevant to the operation of the composition of the invention can be contained in the inventive formulation itself, or they may be derived from other foodstuffs.

Also provided by the present invention is a method for modulating sugar metabolism in a mammalian subject. The method includes administering to the subject a composition of the invention, thereby modulating sugar metabolism of the subject. The method also includes making a composition of the invention available to the subject for ingestion, for instance by providing it through retail outlets or through a dispensing physician or other health care provider. The compositions may be provided per se, or may be contained in food supplements or food products. In a preferred embodiment, the moderating results in a decrease of the rate of sugar metabolism relative to the rate in the absence of a composition of the invention. In another preferred embodiment, the moderating includes a linearization of the rate of metabolism, eliminating spikes and/or valleys in the sugar metabolism profile, and/or decreasing the peak height and/or valley depth in the sugar metabolism profile. In another preferred embodiment, the sugar metabolism is modulating by the composition effecting a decrease in the absorption rate of the sugar by the mammalian gut.

In another embodiment of the present invention, the carbohydrate modifying formulation includes a natural sweetener formulation as a dry, anhydrous, white, powder that can be included or added to any beverage or foodstuff that the consumer desires to sweeten. As used herein, the natural sweetener formulation is a sweetener that does not include any molecules that are not naturally occurring in nature. More specifically, the sweetener formulation comprises crystalline fructose and a natural intense sweetener, and a carbohydrate modifying agent. Crystalline fructose is included in order to provide a sweet taste that is similar to table sugar (sucrose), but at the same time does not provoke an insulin response as readily as sucrose. The intense sweetener is included in the sweetener formulation in order to augment the sweet taste of the crystalline fructose without adding any calorific value to the formulation. This augmentation is necessary because the amount of crystalline fructose that can be included in a given serving size of the sweetener formulation is limited by the inclusion of the carbohydrate modifying agent. The natural intense sweetener can be selected from several commercially available natural intense sweeteners. For example, Cweet®, Magnasweet®, Talin®, and Oh So Sweet®, which do not contain any ingredients other than natural intense sweeteners, can be used with the formulation. Other natural sweeteners like Citrisweet®, which also contains crystalline fructose and oligofructose, can be used as a secondary source of crystalline fructose and oligofructose (an ingredient contained in the carbohydrate modifying agent discussed below), as well as a primary source of a natural intense sweetener.

The carbohydrate modifying agent within the natural sweetener formulation comprises an active soluble fiber, a plurality of antioxidant containing botanical extracts, one or more vitamins, and one or more minerals. In another embodiment, a probiotic, preferably bacillus coagulans can be added to the carbohydrate modifying agent. With respect to the "active soluble fiber", the term refers to a soluble fiber that is biologically responsive to bacteria in the mammalian GI tract and/or participates in one or more blood sugar modifying mechanisms in vivo. The active soluble fiber can be from any source, however, preferred fibers are those that participate in one or more blood sugar modifying mechanism, such as: 1) conversion of the soluble fiber into short chain fatty acids (SCFAs) by the intestinal bacteria (SCFA, particularly propionic acids, increase glycolysis and reduces gluconeogenesis thus normalizing blood sugar); and (2) slowing of the absorption of sugar from the intestinal tract by the soluble fiber, which ultimately influences the rate of sugar metabolism. The most preferred active soluble fiber is an anhydrous oligosaccharide, such as oligofructose.

The plurality of antioxidant containing botanical extracts preferably comprises cinnamon, Golgi berry, bittermelon, and grape seed. These botanical extracts perform three primary functions in the body of a mammal: 1) produce antioxidants that can be used to inhibit and remove free radicals from the blood stream; 2) assist in inhibiting glycation so that mammalian cells are more readily able to metabolize sugar; and 3) facilitate insulin performance. In this regard, it is believed that the botanical extracts exhibit a synergistic relationship with the active soluble fiber oligofructose. When the oligofructose enters the intestinal tract, intestinal flora rapidly metabolizes the oligofructose into short chain fatty acids. This metabolism occurs more rapidly than it does with other types of active soluble fibers. As a result, the short chain fatty acids are ultimately delivered to the blood stream and to cellular structures much faster than they would be delivered if other active soluble fibers were used instead of oligofructose. This rapid deployment of the short chain fatty acids to cellular structures is very beneficial because the fatty acids, along with the mammal's immune system, act to remove free radicals that are produced during cellular metabolism.

In addition, some of the botanical extracts have a synergistic relationship inter se. It is believed that of the four botanical extracts cinnamon is the most active compound in facilitating insulin performance. As a result, it would be beneficial to enhance the activity of cinnamon. In this regard, the inventors further believe that the compound procyanidin in grapeseed extract and the compound anthocyanin in Golgi berry extract act together to enhance the action of cinnamon in the body, giving rise to an unexpected increase in the activity of cinnamon in facilitating insulin performance.

The probiotic within the carbohydrate modifying agent compound is included in order to assist in maintaining a healthy digestive tract and a strong immune system. Most preferably, the probiotic is Bacillus coagulans, which does not need to be refrigerated and is effective in surviving the harsh stomach acids before entering the intestinal tract. When the probiotic reaches the intestinal tract its spores germinate and colonize in the intestines, thereby creating a healthier bacterial flora. Importantly, it is believed that the Bacillus coagulans acts as a catalyst in causing the oligofructose and botanical extracts to form a more robust and biologically active fermentation complex within the intestinal tract than the oligofructose and botanical extracts would otherwise form without the contribution of the probiotic. The more biologically active fermentation complex, in turn, enhances the rate at which the oligofructose is converted into short chain fatty acids and to thereby slow the absorption of fructose from the crystalline fructose into the blood stream. This more robust fermentation complex also acts to enhance the ability of the botanical extracts to perform their functions in the body as described above.

The vitamins included within the carbohydrate modifying agent are most preferably vitamins B12, B6, B3 (niacinamide), biotin, folic acid, and/or vitamin C, and the minerals are preferably chromium and/or selenium. The B vitamins are included in the agent because they are active in the metabolism of carbohydrates and act synergistically with oligofructose that acts to modulate the rate of sugar absorption into the blood stream from the GI tract. Vitamin C provides essential antioxidant functions in the body. Selenium is an antioxidant that helps to prevent free radical formation during cellular metabolism, while chromium assists insulin at the cellular level making it more efficient in removing glucose from the blood and providing the glucose to cells for metabolism.

Upon ingestion by a mammal, the formulation acts to modulate sugar metabolism, which results in a decrease of the rate of sugar metabolism in the person's body relative to the person's metabolism rate that is not being modulated by the formulation. The modulation of sugar by the formulation can also include a linearization of the rate of metabolism, eliminating spikes and/or valleys in the person's sugar metabolism profile, and/or decreasing the peak and/or valley depth in the sugar metabolism profile. The formulation can also be used to modulate sugar metabolism by decreasing the absorption rate of the sugar in the mammal's intestinal tract.

Another feature of the natural sweetener formulation is that the formulation has been developed and its ingredients have been selected in order to provide a level of sweetness that is approximately equivalent to the level of sweetness of granular sucrose or common table sugar. The inventors utilized standard industry methodology of sensory evaluation to compare levels of sweetness and flavor intensity of the natural sweetener formulation to sucrose. The sweetener formulation was compared to sucrose in two different environments: in distilled hot water (110-120° F.) and in distilled cold water (50-55° F.). In order carry out the comparison different quantities of each product were used. For sucrose, which was the control, two sample quantities were used: 1 tsp (4 grams) was added to 100 mls of both hot and cold distilled water, and 2 tsp (8 grams) was similarly added to 100 mls of hot and cold distilled water. For the sweetener formulation, the sample quantities that were used in the comparison to sucrose were: 0.5 grams, 1.0 grams, 1.5 grams, 2.0 grams, and 2.5 grams, with each quantity added to 100 mls of hot and cold distilled water, respectively. A panel of seven lay persons was used to evaluate both sweetness and flavor intensity of the samples in a series of blind taste tests. Five of the panelists routinely used sugar substitutes as their sweetener of choice, and two panelists used only table sugar as their sweetener of choice. At the conclusion of the tests, it was determined by the panelists that, for 2 grams of the sweetener formulation and 8 grams of sucrose, the level of sweetness on scale of 0 to 5, with 0 being the lowest level of sweetness and 5 being the highest, the sweetener formulation and sucrose each had a level of sweetness of 4.0 in cold water and a level of sweetness for the formulation and sucrose of 3.43 and 2.79, respectively, in hot water. For the same quantities of the sweetener and sucrose, the panelists also found that the formulation and sucrose had a flavor intensity of 3.71 and 3.86, respectively, in cold water and a flavor intensity of 2.93 and 2.29, respectively, in hot water. These results demonstrate that the levels of sweetness and flavor intensity for 2 grams of the sweetener formulation are approximately equivalent to the levels of sweetness and flavor intensity for 8 grams (2 tsp) of sucrose.

Before the inventors were able to demonstrate the approximate equivalence of the sweetener formulation to sucrose based upon levels of sweetness and flavor intensity, they subjected numerous different concentrations of the ingredients contained in the sweetener formulation to sweetness and flavor intensity evaluation. Ultimately, the above described equivalence between 2 grams of the formulation and 8 grams of sucrose was successfully demonstrated when the formulation's ingredients were provided in the following concentrations: crystalline fructose in a concentration of about 31.3% by weight of the formulation; an active soluble fiber, preferably oligofructose, in a concentration of about 62.1% by weight of the formulation; antioxidant containing botanical extracts in a concentration of about 0.5% by weight of the formulation, with the extracts of cinnamon, Golgi berry, bittermelon, and grapeseed included in approximately equal amounts; vitamin C, vitamin B12, vitamin B6, vitamin B3, biotin and folic acid in a concentration of about 0.3%, 0.00015%, 0.005%, 0.03%, 0.00075% and 0.001%, respectively, by weight of the formulation; chromium and selenium in a concentration of about 0.00018% and 0.00105%, respectively, by weight of the formulation; a probiotic, preferably bacillus coagulans, in a concentration of about 0.35% by weight of the formulation; an anti-caking compound, preferably Syloid 244, and a starch based filler, preferably Maltodextrin M100, included in concentrations of about 0.15% and 0.263%, respectively, by weight of the formulation; and masking agents in a concentration of about 5% by weight of the formulation. In addition to these ingredients, the formulation contains a natural intense sweetener. In the preferred embodiment, the inventors selected Citrisweet® because the product also contains a source of crystalline fructose and oligofructose, which are included in the concentration percentages of those ingredients listed above. The concentration of the intense sweetener component of Citrisweet® is negligible as compared to the concentrations of the other ingredients in the sweetener formulation. However, any of other natural intense sweeteners that only contain an intense sweetener component could also be used and would similarly not contribute more than a negligible concentration to the concentrations of the other ingredients in the formulation.

The equivalency of the sweetener formulation and sucrose based upon levels of sweetness and flavor intensity allow the formulation to be packaged and marketed as a table sugar replacement, but with the additional feature of having the carbohydrate modifying benefits described above that are not possible with table sugar. For example, a serving size of 2 grams of the natural sweetener formulation can be added to a disposable packet which can be used by a consumer to sweeten beverages and other foodstuffs in the same manner that the consumer would use a serving size of 8 grams or 2 teaspoons of table sugar.

The following examples are provided to solely illustrate some specific applications of the sweetener and carbohydrate modifying formulation and are not intended to describe any additional limitations. Persons skilled in the art will readily recognize a variety of non-critical parameters that could be changed or modified to yield essentially similar results.

Examples

Example 1

Yogurt Drink (8 Oz)

Combine yogurt cultured milk, fresh fruit and sugar (10 g) or intense sweetener of choice (10 ppm) with the modifying agent. The modifying agent includes inulin fibers (3 g), bilberry, citrus bioflavonoid, green tea extract mix (polyphenolic) (100 mg); soy isoflavones (50 mg); zinc sulfate (7 mg); and vitamin C (60 mg). Add sufficient water to bring volume to 8 ounces.

Example 2

Soft Drink (8 Oz)

Combine water (still or carbonated) flavor (natural or artificial) and sugar (10 gm) or an intense sweetener of choice (10 ppm) with the modifying agent.

The modifying agents includes inulin fiber (3 g), bilberry, citrus bioflavonoids, green tea extract mix (polyphenolic) (100 mg); soy isoflavones (50 mg); zinc sulfate (7 mg); and vitamin C (60 mg); soy protein extract (50 mg): and mineral amino chelates (amino acid glycine) (300 mg).

Example 3

Natural Sweetener Formulation (2 Gram Serving) for Beverages and Foodstuffs

Create a 2 gram serving size of the natural sweetener formulation in the form of a dry, anhydrous, white, powder by combining by mixing oligofructose (0.821 g); crystalline fructose (0.346 g); a botanical blend containing extracts of cinnamon, Golgi berry, bittermelon, and grapeseed (0.010 g) with equal amounts of each botanical included in the blend; Vitamin Premix FT090140 by Fortitech containing vitamins C (6 mg as ascorbic acid), B12 (0.3 mcg as Cyanocobalamin), B6 (0.1 mg as Pyridoxine), B3 (0.6 mg as niacinamide), biotin (15 mcg), folic acid (20 mcg), chromium (3.6 mcg as chromium chloride), selenium (2.1 mcg as sodium selenite), the anti-caking agent Syloid 224 (3 mg), and the starch based filler Maltodextrin M100 (5.5 mg); Bacillus coagulans (0.007 g); Citrisweet® (0.701 g); taste masking agent Simply Rich 121 (0.077 g) by Lifewise Ingredients, LLC, and masking agent #060861 (0.023 g) by Kerry Group plc.

The 2 gram serving size of sweetener formulation can be used to sweeten any hot or cold beverage that a consumer desires to sweeten. For example, the 2 gram serving size of the formulation, which is equivalent in sweetness and flavor intensity to approximately 8 grams or 2 teaspoons of table sugar (i.e. sucrose), can be added to coffee, tea, unsweetened hot cocoa in hot milk in order to make hot chocolate, unsweetened lemon juice in order to make lemonade, unsweetened carbonated flavor waters, unsweetened protein powder energy drinks made with milk, water, juice yogurt, or soy milk. In addition, for ease of use, the 2 gram serving size of the formulation can be provided in small disposable packets, similar to table sugar packets that contain approximately 2 teaspoons of sugar.

Although the sweetener and carbohydrate modifying formulation of the present invention has been described in several embodiments, it will be recognized by those skilled in the art that other embodiments and features may be provided without departing from the underlying principals of those embodiments. The scope of the invention is defined by the appended claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

The invention claimed is:

1. An anhydrous table sugar replacement product, comprising:
    crystalline fructose in a concentration of approximately 31% by weight of the product;
    a natural intense sweetener; and
    a carbohydrate modifying agent comprising:
        oligofructose as an active soluble fiber in a concentration of approximately 62% by weight of the product;
        antioxidant containing botanical extracts selected from the group consisting of extracts of cinnamon, golgi berry, bittermelon and grapeseed in concentrations totaling approximately 0.5% of the product;
        vitamins selected from the group consisting of C, B12, B6, B3, biotin and folic acid in a concentration totaling approximately 0.3% by weight of the product;
        minerals selected from the group consisting of chromium and selenium;
    an anti-caking compound, a filler and a masking agent in a concentration totaling approximately 5.5% by weight of the product;
    whereby approximately 2 grams of the product has levels of sweetness and flavor intensity that are approximately equivalent to the levels of sweetness and flavor intensity of approximately 8 grams of sucrose; and
    whereby after the product is ingested, the carbohydrate modifying agent: slows the rate of absorption of fructose derived from the crystalline fructose into the bloodstream; decreases the rate of gluconeogenesis; modulates the manner in which cells use glucose; and in combination with the crystalline fructose and natural intense sweetener, substantially increases the antioxidant capacity within the body due to an unexpected synergy between the crystalline fructose, natural intense sweetener, active soluble fiber, botanical extracts, vitamins, and minerals.

2. The product of claim 1 which is in the form of a dry, white, powder.

3. The product of claim 1 in which the natural intense sweetener augments the level of sweetness of the crystalline fructose.

* * * * *